United States Patent [19]

Schmidt

[11] Patent Number: 4,642,406
[45] Date of Patent: Feb. 10, 1987

[54] HIGH SEVERITY PROCESS FOR XYLENE PRODUCTION EMPLOYING A TRANSALKYLATION ZONE FOR XYLENE ISOMERIZATION

[75] Inventor: Robert J. Schmidt, Rolling Meadows, Ill.

[73] Assignee: UOP Inc., Des Plaines, Ill.

[21] Appl. No.: 775,982

[22] Filed: Sep. 13, 1985

[51] Int. Cl.$^4$ .............................................. C07C 5/22
[52] U.S. Cl. .................................. 585/477; 585/475; 585/478; 585/481
[58] Field of Search ............... 585/477, 478, 481, 475

[56] References Cited

U.S. PATENT DOCUMENTS

| | | | |
|---|---|---|---|
| 3,211,798 | 10/1965 | Burk, Jr. et al. ........................ | 260/668 |
| 3,409,686 | 11/1968 | Mitsche ............................... | 260/668 |
| 3,464,929 | 9/1969 | Mitsche ............................... | 252/442 |
| 3,525,775 | 8/1970 | Bolton et al. ............................ | 260/668 |
| 3,636,180 | 1/1972 | Broughton ........................ | 260/668 A |
| 3,637,881 | 1/1972 | Williams et al. .................. | 260/668 A |
| 3,696,107 | 10/1972 | Neuzil .............................. | 260/674 SA |
| 3,701,813 | 10/1972 | Stenmark ........................ | 260/668 A |
| 3,780,121 | 12/1973 | Suggitt et al. ..................... | 260/672 T |
| 3,780,122 | 12/1973 | Pollitzer ........................ | 260/672 T |
| 3,996,305 | 12/1976 | Berger ........................... | 260/672 T |
| 3,996,306 | 12/1976 | Korous et al. ................. | 260/674 SA |
| 4,041,091 | 8/1977 | Henry ........................... | 260/672 T |
| 4,083,886 | 4/1978 | Michalko ....................... | 260/672 T |
| 4,101,596 | 7/1978 | Mitchell et al. ................. | 260/668 A |
| 4,341,914 | 7/1982 | Berger .......................... | 585/474 |
| 4,381,419 | 4/1983 | Wylie ........................... | 585/828 |
| 4,423,279 | 12/1983 | Kulprathipanja .................. | 585/828 |

Primary Examiner—Curtis R. Davis
Attorney, Agent, or Firm—Thomas K. McBride; John F. Spears, Jr.

[57] ABSTRACT

A process is disclosed for the production of high quality benzene and a desired xylene isomer, preferably paraxylene, from a mixture of $C_7$-plus alkylaromatic hydrocarbons. The desired xylene isomer is recovered by absorptive separation from a stream of two or three xylene isomers. The resultant isomer-depleted stream is passed into a transalkylation zone together with both feed and recycled toluene and $C_9$ aromatic hydrocarbons instead of being passed into a xylene isomerization zone. Benzene and xylenes are fractionated from the transalkylation zone effluent stream, with the xylenes being passed into the absorptive separation zone. A nonmetal catalyst is employed in the transalkylation zone, which must be operated at high severity (high temperature) conditions.

13 Claims, 1 Drawing Figure

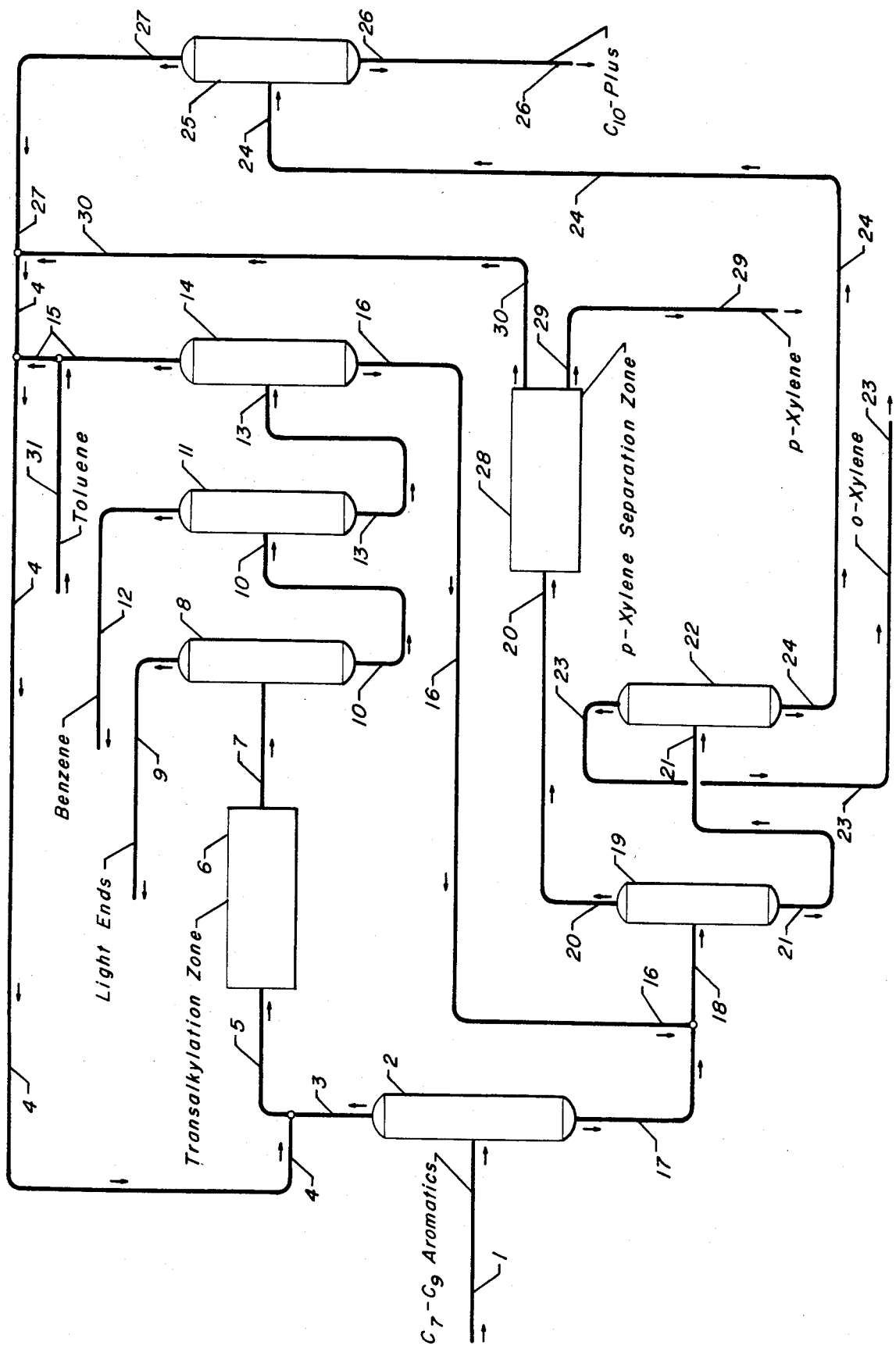

HIGH SEVERITY PROCESS FOR XYLENE PRODUCTION EMPLOYING A TRANSALKYLATION ZONE FOR XYLENE ISOMERIZATION

FIELD OF THE INVENTION

The invention relates to a hydrocarbon conversion process in which $C_8$ alkylaromatic hydrocarbons are produced. The invention also relates to an integrated process employing a catalytic reaction step in which a preferred xylene isomer is produced by a rearrangement reaction of other xylene isomers and a separation step in which the preferred xylene isomer is recovered by adsorptive separation from a mixture containing several xylene isomers. The invention also specifically relates to the transalkylation of $C_9$ and $C_7$ alkylaromatic hydrocarbons for the production of xylenes. The invention is specifically concerned with the overall process flow employed to produce additional amounts of the desired xylene, rather than the specific catalyst or apparatus employed in the process.

INFORMATION DISCLOSURE

The production of specific xylene isomers is an important petrochemical process. For instance, large quantities of paraxylene are consumed as the feed chemicals in processes leading to the production of polyesters used in clothing manufacture. The importance of being able to obtain high purity streams of one particular xylene isomer has led to the development of a number of separation techniques. For instance, it is widely known that paraxylene may be separated from a mixture of two or more xylene isomers through partial crystallization. This separatory technique is employed in some industrial processes. A large amount of paraxylene is also recovered through the use of adsorptive separation techniques such as described in U.S. Pat. Nos. 3,696,107 issued to R. W. Neuzil; 3,996,306 issued to D. J. Korous; 4,381,419 issued to R. Wylie; and 4,423,279 issued to S. Kulprathipanja. These references describe suitable absorbents and operating techniques for the preferred method of recovering the desired xylene isomer as that step is performed in the subject process.

The ability to selectively remove one of the xylene isomers led to the development of xylene isomerization processes such as described in U.S. Pat. Nos. 3,409,686 and 3,464,929 both issued to R. T. Mitsche and 4,101,596 issued to K. M. Mitchell et al. The latter reference is also pertinent for its showing that $C_8$ hydrocarbons recovered from the effluent of the isomerization zone by fractional distillation may be recycled to a paraxylene removal zone. This integration of the two steps of paraxylene isomerization and paraxylene separation are also shown in U.S. Pat. Nos. 3,636,180 issued to D. B. Broughton.

The higher commercial value of xylenes as compared to toluene and $C_9$ alkylaromatics has prompted the development of transalkylation processes, sometimes referred to as disproportionation processes, which produce xylenes from a feed stream of $C_7$ or $C_7$ and $C_9$ hydrocarbons. Transalkylation processes and catalysts are described in U.S. Pat. Nos. 3,780,122 issued to E. L. Pollitzer; 3,996,305 issued to C. V. Berger; and 4,083,886 issued to E. Michalko. The Berger reference illustrates the fractionation of the transalkylation zone effluent stream to produce a $C_8$ alkylbenzene product stream and a recycle stream of toluene and $C_9$ alkylbenzenes which are returned to the transalkylation zone.

A number of flow schemes which incorporate xylene isomerization, xylene separation, fractionation, and transalkylation into a single process have been developed. For instance, U.S. Pat. No. 3,211,798 issued to E. H. Burk Jr. et al describes a process wherein both transalkylation and xylene isomerization are performed in a single moving bed reactor system. The same catalyst is therefore employed for both the transalkylation and isomerization reactions, with the feed points of the material to be isomerized and to be translakylated and the conditions being chosen to promote the desired reactions. The use of synthetic gel catalysts and catalysts containing silica or silica and alumina are disclosed. This reference is believed not to teach the charging of an external toluene feed stream to the reaction zones. The reference sugggests temperatures of from 800 to 975 degrees Fahrenheit (426 to 523 degrees Centigrade) for transalkylation.

Other references which describe the use of isomerization, transalkylation and xylene recovery in a single process include U.S. Pat. Nos. 3,701,813 issued to D. G. Stenmark; 4,041,091 issued to M. J. Henry; and 4,341,914 issued to C. V. Berger. In the Berger reference, xylenes recovered from the feed stream and xylenes recovered by fractionation from the transalkylation zone effluent stream are both passed into a paraxylene separation-xylene isomerization loop.

U.S. Pat. No. 3,525,775 issued to A. P. Bolton et al is pertinent for its teaching that disproportionation (migration of methyl groups from one ring to another ring) also occurs during the isomerization of xylenes. The reference also states in column 6 that a toluene-benzene fraction, a tri and higher methyl benzene fraction, and unrecovered xylene isomers can be recycled to the product separation zone and combined with the feedstock. This is described as increasing the efficiency of utilization of the meta-xylene. The reference in column 4 et seq. describes the action caused in mildly "coking" the catalyst. This coking suppresses disproportionation of xylene, which appears to be considered as very beneficial to the overall process.

The Bolton reference also describes, in column 2, that the prior systems employing a noble-metal on alumina or silica-alumina supports in the presence of hydrogen should be operated above 800 degrees Fahrenheit (426 degrees Centigrade) and preferably above 850 degrees F. (454 degrees Centigrade) to limit the hydrogenation of the aromatic feed and products to napthenic compounds.

U.S. Pat. No. 3,637,881 issued to A. H. Williams et al describes a process for isomerizing alkylaromatic hydrocarbons with a catalyst comprising a Group VIII noble metal. The reference indicates that the transalkylation of $C_8$ aromatics will occur simultaneously with the isomerization. U.S. Pat. No. 3,780,121 issued to R. M. Suggitt et al describes a process for the disproportionation of alkylaromatics in the presence of a catalyst comprising hydrogen mordenite and a Group I-B metal. The process operates at mild temperatures (up to 399 degrees Centigrade). The reference indicates that the isomerization of orthoxylene will occur simultaneously with orthoxylene disproportionation.

BRIEF SUMMARY OF THE INVENTION

The invention provides a process for the production of a desired xylene isomer from a first feed stream containing toluene and second feed stream containing one or more of the other xylene isomers. The subject process reduces required capital investment by eliminating the need for a separate xylene isomerization reactor system and by reducing the required amount of fractional distillation equipment. The subject process is believed to have yield advantages over prior art systems which include both isomerization and transalkylation reaction zones because the aromatics ring loss normally encountered in a passage through a transalkylation zone is less than that which is expected in the xylene isomerization reaction zone. The subject process should therefore reduce the amount of undesired light and heavy hydrocarbon by-products per unit volume of xylene isomer produced. The subject process also produces a very high quality benzene product stream. These improvements are achieved by passing the raffinate stream of the xylene separation zone into the transalkylation zone, preferably in admixture with the $C_7$ and $C_9$ aromatic feeds normally charged to the transalkylation zone. The transalkylation reaction zone therefore also functions as an isomerization zone. A catalyst which is free of noble metals is employed at high severity operating conditions to achieve the desired products.

A broad embodiment of the subject invention may be characterized as a process for the production of a desired xylene isomer which comprises the steps of: passing a hereinafter characterized first process stream, which comprises at least two xylene isomers, into an adsorptive xylene separation zone, withdrawing a product stream comprising the desired xylene isomer from the xylene separation zone and also withdrawing a raffinate stream comprising an undesired xylene isomer from the xylene separation zone; passing a first feed stream comprising toluene, a hereinafter characterized recycle stream and at least a portion of the undesired xylene isomer content of the raffinate stream into a catalytic transalkylation zone containing a nonmetal transalkylation catalyst and operated at high severity conditions including a temperature over 426 degrees Centigrade, and forming a transalkylation zone effluent stream which comprises benzene, toluene, xylenes and $C_9$ aromatics; separating the transalkylation zone effluent stream by fractional distillation to yield a benzene-rich process stream, a toluene-rich process stream, a xylene-rich process stream comprising two xylene isomers, and a second process stream comprising $C_9$ aromatics; recycling at least a portion of the toluene-rich process stream into the transalkylation zone as said recycle stream; and passing at least a portion of the xylene-rich process stream into the xylene separation zone as said first process stream.

BRIEF DESCRIPTION OF THE DRAWING

The drawing is a simplified flow diagram showing a preferred embodiment of the invention. $C_7$ to $C_9$ aromatics entering the process through line 1 are separated in a prefractionator 2 to yield a xylene containing fraction fed to a fractionation train of columns 19 and 22 and toluene passed through line 3 to the transalkylation zone 6. Orthoxylene is removed by fractionation and the remaining xylene isomers pass as a xylene-rich stream into the xylene separation zone 28 wherein paraxylene is recovered for removal through line 29. A paraxylene depleted raffinate stream comprising some orthoxylene and metaxylene is passed through lines 30 and 4 into the transalkylation zone. The transalkylation reaction zone affects both the conversion of toluene and $C_9$ alkylaromatics to xylenes and also establishes an equilibrium concentration of the various xylene isomers. The transalkylation zone effluent stream is fractionated to yield a xylene-containing stream carried by line 16, which transfers the just produced paraxylene to the separation zone via column 19.

DETAILED DESCRIPTION

Toluene and $C_9$ alkylaromatic hydrocarbons are presently produced at a much greater rate than is required to satisfy the demand for these hydrocarbons as reactants or products. There is however relatively strong and increasing demand for various xylenes, especially paraxylene. As already pointed out, xylenes are very valuable as feedstocks for many widely used petrochemicals and plastics. For instance, orthoxylene is used in the production of phthalic anhydride.

As set out above, various commercial processes have therefore been developed which convert toluene and $C_9$ alkylaromatics into xylene. These processes involve such molecular rearrangement as the transfer of the methyl groups of toluene to form benzene and xylenes or the transfer of the methyl groups of toluene and trimethylbenzenes to produce xylenes. Other $C_9$ aromatics may undergo other types of reactions. For example, ethyl groups may be transalkylated or dealkylated. These processes are sometimes referred to as disproportionation, but are referred to herein as transalkylation processes. Transalkylation thereby can be used to produce a mixture of xylene isomers. As also set out above, heretofore a desired xylene isomer has been separated out of the transalkylation effluent and the remaining isomers then passed through an isomerization zone to produce more of the desired xylene isomer.

The economic viability of any process for the production of xylenes is dependent on several factors. One of the most important of these is the total yield of the desired xylene isomer. An excessive production of undesired by-products places a heavy economic burden on a process. Another important economic factor in the success of a commercial process is the initial capital cost of the equipment and catalyst necessary. Finally, the overall operating cost of the process includes such utility items as heating and cooling streams associated with reactors and fractionation columns and the energy expended in compressing or pumping various fluid streams. It is an objective of the subject invention to provide a highly efficient process for the production of a desired xylene isomer. It is another objective of the subject invention to reduce the capital cost of a process for the production of paraxylene from a mixture of $C_7$ to $C_9$ aromatics. It is a further objective of the invention to reduce the utilities cost of operating a process for the production of paraxylene from a mixture of $C_7$ to $C_9$ alkylaromatic hydrocarbons.

It has now been found that the required xylene isomerization can be performed within a transalkylation zone employing a nonnoble metal transalkylation catalyst. It is therefore unnecessary to provide a separate catalytic xylene isomerization reaction zone. This significantly lowers the complexity and cost of the process. An additional advantage is that the "ring loss" of aromatic compounds during passage through the transalkylation zone is much less than during passage through a xylene isomerization zone. The overall yield of the process is therefore greater than a process employing both isomerization and transalkylation zones.

The feed stream or streams to the subject process may take several forms. The feed stream preferably contains $C_7$-plus alkylaromatic hydrocarbons such as toluene, the various xylenes, and $C_9$ alkylaromatics such as trimethylbenzenes. These aromatic hydrocarbons can be obtained from a wide variety of sources such as by the liquefaction of coal, thermal cracking operations designed to produce olefinic hydrocarbons, and by extraction from crude oil fractions. The most widely used and preferred source of the feed aromatic hydrocarbons is a liquid-liquid extraction zone in which the aromatic hydrocarbons are selectively removed from a feed mixture having a selective boiling point range and containing a mixture of aromatic and nonaromatic hydrocarbons. A typical sequence for the production of the desired feed hydrocarbons therefore includes the fractionation of a naphtha boiling range hydrocarbon mixture from a crude oil stream, the hydrotreatment of this fraction for the removal of sulfur, nitrogen, and other undesired compounds, the catalytic reforming of this fraction to increase the aromatic content, and a liquid-liquid extraction of the aromatics produced in this manner. The aromatics could also be separated from a wide boiling range reformate by extraction and fractionation.

The feed stream may contain a full boiling range mixture of $C_7$ to $C_9$ aromatics and be fed into a prefractionation column in the manner shown in the drawing. This column would then divide the single entering feed stream into a toluene-rich stream destined for transalkylation and a $C_8$-plus stream containing xylenes. Alternatively, the feed hydrocarbons may be charged to the process in different manners. For instance, the subject process could be operated with a feed stream containing only $C_7$ and $C_9$ alkylaromatics being passed directly into the transalkylation zone. It is also possible that the transalkylation zone may receive a high purity toluene-rich feed stream with all of the xylenes being produced within the transalkylation zone. A third possibility is the passage of separate feed streams rich in toluene and xylenes or xylenes and $C_9$ alkylaromatics into the process. A toluene feed stream comprising mainly benzene and toluene would preferably be charged to the column producing the benzene product stream as a net overhead.

Those skilled in the art of hydrocarbon conversion process design will also recognize that it is possible for the feed streams to enter the process at a wide variety of different points depending on its composition. That is, the optimum point for the feed materials to enter the process will be dependent upon its composition and fractionation scheme which is employed in the process. The feed stream(s) may therefore be admixed with the transalkylation zone effluent stream, with the paraxylene separation zone raffinate stream or to be passed into one of the other fractionation columns illustrated in the drawing instead of column 2. For instance, a toluene feed stream from an external source may be charged into the fractionation column, or an upstream column, which is preparing the toluene-containing recycle stream. At least 10 mole percent, and preferably at least 15 mole percent of the total hydrocarbons charged to the process as fresh feed is toluene.

Heretofore integrated petrochemical complexes designed to convert a mixture of $C_7$ to $C_9$ alkylaromatic hydrocarbons to a single xylene would employ both a catalytic xylene isomerization zone and a catalytic transalkylation zone. The effluent from each zone would be fractionated to yield a xylene mixture then charged to the xylene separation zone. The subject process employs only a single catalytic reaction zone.

In the subject process both transalkylation of toluene and $C_9$ alkylaromatics to xylenes and xylene isomerization are performed simultaneously in the same reaction zone. This is one distinguishing feature of the subject process. The invention is characterized by the charging of a considerable amount of both toluene and xylenes as fresh feed, the use of a noble metal-free catalyst and the operation of the single reaction zone at high severity temperature conditions as described below.

The operation of the subject process may be readily discerned by reference to the drawing. In the drawing, a single feed stream comprising an admixture of toluene, xylenes, and various $C_9$ aromatic hydrocarbons is passed into a first fractionation column 2 through line 1. This column functions as a deheptanizer which removes overhead substantially all of the toluene entering the column while the heavier or less volatile xylenes and $C_9$ aromatics are removed as a bottoms liquid stream through line 17. The net overhead of column 2 carried by line 3 is therefore admixed with the contents of line 4 and passed into the transalkylation zone 6 through line 5. Line 4 carries the xylene-rich raffinate of the xylene separation zone 28 and $C_9$ alkylaromatics from fractionation column 25. Within the transalkylation zone, the entering hydrocarbons are heated and vaporized and contacted with a solid noble metal-free transalkylation catalyst in a reaction zone in admixture with hydrogen. This action is effective to create additional amounts of xylenes from the entering hdyrocarbons by the transalkylation of the toluene and $C_9$ hydrocarbons and to isomerize xylenes charged to this zone and produced in this zone such that the effluent of the transalkylation zone will contain a substantially equilibrium concentration admixture of the various xylene isomers. The transalkylation zone effluent stream will also contain residual toluene, benzene formed during the transalkylation reaction, and various light ends such as methane, ethane, and propane produced within the reaction zone. The transalkylation zone effluent stream, after partial condensation and separation of hydrogen-rich gas, is passed through line 7 into a light ends column 8. The light $C_5$-minus hydrocarbons and any dissolved hdyrogen are removed overhead as a net overhead stream withdrawn from the process through line 9. The remaining $C_6$-plus hydrocarbons are removed from column 8 as a net bottoms stream transfered through line 10 to the benzene column 11.

Benzene column 11 is designed and operated to remove essentially all of the benzene which enters this column as a net overhead product stream removed from the process in line 12. The remaining $C_7$-plus hydrocarbons are passed through line 13 into the toluene column 14. The material flowing into column 14 is basically the $C_7$-plus portion of the effluent of the transalkylation zone plus any added $C_7$-plus hydrocarbons. A separate toluene feed stream not shown may be fed into line 10, column 11, line 13 or column 14. The exact point of addition will depend on such factors as the benzene content of the toluene feed stream. These hydrocarbons are separated into a $C_8$-plus portion which is rich in xylenes removed as a net bottoms stream of the column through line 16 and a net overhead stream comprising toluene removed through line 15. The toluene-rich net overhead stream is recycled to the transalkylation zone through line 4. A separate toluene rich feed stream may be fed to the process by admixture into the overhead stream of the toluene column 14 through line 31.

The $C_8$-plus fraction removed from column 2 via line 17 and the $C_8$-plus fraction removed from column 14 are admixed and passed via line 18 into a column 19 which functions as a xylene stripping column. The net bottoms stream removed from this column in line 21 comprises the less volatile orthoxylene and $C_9$-plus aromatic hydrocarbons fed to the column. This bottoms stream is passed through line 21 into the orthoxylene column 22. The net overhead stream of the orthoxylene column removed through line 23 is a high-purity stream of orthoxylene which is withdrawn from the process as an optional product stream produced in this specific embodiment. The remainder of the hydrocarbons which enter the orthoxylene fractionation column 22 are concentrated into a net bottoms stream removed through line 24 and passed into the Chd 9 stripping column 25. This relatively small capacity column separates the entering hydrocarbons into a net overhead stream which is rich in the $C_9$ aromatics and withdrawn through line 27 and a net bottoms stream which contains the $C_{10}$-plus hydrocarbons which enter the column and is withdrawn through line 26. The $C_{10}$-plus hydrocarbons may be present in the feed stream or streams charged to the process or due to the formation of $C_{10}$-plus hydrocarbons in the transalkylation zone. The $C_9$ aromatics of the overhead stream 27 are recycled to the transalkylation zone in admixture with toluene from line 15 via lines 4 and 5.

The xylene-rich net overhead stream of the xylene stripping column 19 is passed via line 20 into the paraxylene separation zone 28. In this zone, the entering xylenes are preferably contacted with a fixed bed of a selective absorbent which preferentially retains paraxylene over metaxylene. The unabsorbed xylenes are separated from the desorbent used in the process in fractionation facilities provided within the separation zone. This produces a stream referred to in the art as the separation zone raffinate stream which is preferably rich in metaxylene. This raffinate stream is recycled through lines 30 and 4 to the transalkylation zone 6. The absorbed paraxylene is removed through the use of a desorbent and is then fractionated from the desorbent to produce the xylene-rich product stream withdrawn from the process through line 29.

In an alternative embodiment of the subject process, the orthoxylene column is not employed and the overhead stream of the xylene stripping column 19 contains a near equilibrium concentration of the three xylene isomers. In this instance, the raffinate stream removed from the separation zone 28 will have a high concentration of each of the two undesired xylene isomers. In another variation to the subject flow, the xylene separation zone would be operated to produce a different xylene isomer as the product stream. That is, metaxylene could be removed from the separation zone as the product stream of the process, with paraxylene being recycled through line 30 to the transalkylation zone for the production of additional metaxylene. A further variation to the embodiment shown in the drawing is the provision of fractionation facilities to produce a high-purity stream of pseudocumene or a stream of 1,3,5 trimethylbenzene.

As used herein, the term "substantially all" is intended to indicate an amount over 90 mole percent, and preferably over 95 mole percent, of the total compound or group of compounds referred to in the context of the term's usage. In a similar manner, the term "rich" is intended to indicate a molar concentration over 50 percent, preferably over 65 percent, of the indicated compound or class of compounds. Unless otherwise indicated, the term "transalkylation zone" is used herein to indicate the single catalytic reaction zone employed within the process for the purposes of both transalkylation (conversion of toluene and/or $C_9$ alkylaromatics to xylenes) and the isomerization of xylenes to reestablish an equilibrium xylene isomer concentration. This zone is basically referred to as the transalkylation zone since this function still occurs within the zone, the zone is still preferably operated at the conditions normally employed for transalkylation, and a traditional transalkylation catalyst is employed therein.

A preferred embodiment of the invention may accordingly be characterized as a process for the production of a desired xylene isomer which comprises the steps of: passing a first feed stream comprising at least 35 mole percent toluene, a first process stream, which comprises at least one xylene isomer, and a hereinafter characterized recycle stream which comprises toluene into a catalytic transalkylation zone which contains a nonmetal transalklylation catalyst and is operated at high severity transalkylation conditions including a temperature over 426 degrees Centigrade and producing a transalkylation zone effluent stream which comprises benzene, toluene, xylenes and $C_9$ aromatics; separating the transalkylation zone effluent stream by fractional distillation in a fractional distillation zone and producing a benzene-rich process stream, a toluene-rich process stream, a xylene-rich process stream and a second process stream, which comprises $C_9$ aromatics; removing at least a portion of the benzene-rich process stream as a first product stream; returning at least a portion of the toluene-rich process stream to the transalkylation zone as the previously referred to recycle stream; passing the xylene-rich process stream into an adsorptive xylene separation zone and producing a second product stream, which comprises paraxylene, and a separation zone raffinate stream, which comprises an undesired xylene isomer; and passing at least a portion of the raffinate stream into the transalkylation zone as at least a portion of the first process stream.

The fractional distillation zone preferably is arranged as shown in the drawing and comprises five separate columns. However, as pointed out elsewhere the last column, the ortho xylene column, could be deleted. The composition and source of the xylene-rich stream to be passed into the separation zone is subject to variation. For instance, if the presence of ortho xylene and $C_9$-plus alkylaromatics is acceptable in the xylene separation zone then the streams of lines 16 or 18 could be passed directly into the separation zone 28 as the xylene-rich stream. A feed stream comprising $C_7$ through $C_9$ aromatics is preferably separated in a prefractionation or splitting column 2 as shown on the drawing. Such a combined feed could also be passed into column 14 and split therein into separate feed streams.

It is believed that the equipment necessary to practice the subject invention such as fractionation columns, reactors, control systems, pumps, etc. may be designed, specified and built by those skilled in the art of petroleum/petrochemical process design and construction. Although rather complex, the equipment and adsorbent used in performing the process may be of conventional design similar to that now employed in the petrochemical industry.

Typically, the admixture charged to the transalkylation reaction zone is first heated by indirect heat exchange against the effluent of the reaction zone and is then further heated in a fired heater. The resultant vaporous stream is then passed through the reaction zone, which may comprise one or more individual reactors. The use of a single reaction vessel having a fixed cylindrical bed of catalyst is preferred, but other reactor configurations utilizing moving beds of catalyst or radial flow reactors may be employed if desired. Passage of the feed admixture through the reaction zone effects the production of a vaporous effluent stream comprising hydrogen and both the feed and product hydrocarbons. This effluent is normally cooled by indirect heat exchange against the stream entering the reaction zone and then further cooled through the use of air or cooling water. The temperature of the effluent stream is normally lowered sufficiently to effect the condensation of substantially all of the feed and product hydrocarbons having six or more carbon atoms per molecule. The resultant mixed phase stream is passed into a vapor-liquid separator wherein the two phases are separated. The hydrogen-rich vapor is recycled. The condensate is passed into a stripping column in which substantially all $C_5$ and lighter hydrocarbons present in the effluent are concentrated into an overhead stream and removed from the process. The remaining hydrocarbons are removed as a net stripper bottoms stream which is referred to herein as the transalkylation zone effluent stream.

Sufficient hydrogen is admixed with the hydrocarbons which are passed into the transalkylation zone to form an admixture having a hydrogen to total hydrocarbon mole ratio above 2:1 and preferably above 5:1. The hydrogen to hydrocarbon mole ratio need not exceed 10:1 for successful operation of the process. This admixture is circulated through a bed of solid transalkylation catalyst located within a reaction zone as a vapor stream at an elevated temperature. The conversion which may be achieved wtihin the reaction zone is limited by the thermodynamic equilibrium of the hydrocarbons which are present. For this reason, it is desired that the admixture contains only a small amount of any product hydrocarbon. Preferably, the feed stream contains less than 2 mole percent of any product hydrocarbon.

The conditions normally described for use in the transalkylation reaction zone include a temperature of from about 200 to about 525 degrees Centigrade (about 392 to 977 degreees Fahrenheit). The subject process requires operation at high severity conditions as measured by reaction zone temperature and therefore cannot be performed successfully at the lower temperature portion of this broad range. The temperature required to maintain a desired degree of conversion will increase as the catalyst gradually loses activity during processing. Normal end-of-run temperatures may therefore exceed start-of-run (fresh catalyst) temperatures of 65 Centigrade degrees or more. All reaction zone operating temperatures specified herein are start-of-run temperatures at the reactor inlet. It is essential that the reaction zone is operated at a temperature above 426 degrees Centigrade (800 degrees Fahrenheit). It is preferred that the reaction zone start-of-run temperature is at least 438 degrees Centigrade (820 degrees Fahrenheit) and more preferably at least 443 degrees Centigrade (830 degrees Fahrenheit). Operations must normally be stopped at a temperature of about 487–498 degrees Centigrade (910–930 degrees Fahrenheit) to prevent excessive thermal cracking and catalyst coking.

This high severity operating temperature is necessary to produce high quality benzene. Two factors combine to result in the production of more and better quality benzene at higher reaction conditions. The first factor is that the production of naphthenes is favored at lowered temperatures. This is basically because the naphthenes are not cracked as extensively at lower temperatures. The concentration of $C_7$ nonaromatics (paraffins and naphthenes) which are very difficult to separate from benzene by fractional distillation thereby increases in the transalkylation zone effluent stream as the temperature decreases. These compounds are the basic impurities in benzene. Since it is commercially impractical to remove them by fractionation their initial production must be limited to produce high quality benzene. The second factor which leads to the production of high quality benzene at high severity conditions is the increased rate of benzene production which occurs at higher temperature due to increased amounts of transalkylation. The larger amount of benzene results in more dilution of the nonaromatic impurities.

The following data is presented to show the effect of operating temperature on the rate of benzene impurity production during the transalkylation of a pure toluene feed stream. To allow for comparison of impurity production rates the percentage of toluene conversion was held constant by increasing the space velocity as required. The results were obtained over a metal-free mordenite catalyst at a 4:1 hydrogen to toluene mole ratio. NA stands for nonaromatics that coboil with benzene ($A_6$).

| Test | Temp. | % Tol Conv. | % $A_6$ prod. | ppm NA |
| --- | --- | --- | --- | --- |
| 1 | 399 | 50 | 21.4 | 717 |
| 2 | 410 | 48–49 | 20.5 | 673 |
| 3 | 421 | 49 | 20.2 | 512 |
| 4 | 449 | 48 | 20.6 | 322 |
| 5 | 468 | 48 | 20.5 | 295 |
| 6 | 482 | 48 | 20.4 | 275 |

The temperatures are in Centigrade degrees. The percentage of toluene conversion and benzene yield are in weight percent. The data readily shows the advantage of high severity operations in producing lower contaminant levels.

The reaction zone is operated at moderately elevated pressures broadly ranging from about 1.0 to 60 atmospheres gauge. A preferred pressure range is from 20 to 35 atmospheres. The transalkylation reaction can be effected over a wide range of space velocities. A general range of suitable space velocities is from about 0.2 to about 10.0. A preferred range of space velocities is from 0.5 to 2.0. These ranges refer to liquid hourly space velocities.

A large number of solid transalkylation catalysts have been developed. For instance, U.S. Pat. No. 3,729,521 decribes 27 different catalysts which were tested for transalkylation activity and selectivity. The catalyst providing the best performance was prepared to contain 2.5 wt. % cobalt oxide and 10 wt. % molybdenum trioxide deposited on a support which contained 35 wt. % ultrastable, large-pore crystalline aluminosilicate material suspended in and distributed throughout a matrix of catalytically active alumina. In another embodiment, the ultrastable, large-pore crystalline aluminosilicate material is suspended in an amorphous silica-alumina cracking catalyst. Previously cited U.S. Pat. No. 3,849,340 describes a catalyst useful for the transalkylation of toluene which comprises a zeolite component having a mordenite crystal structure and having a silica to alumina mole ratio of at least 40:1 prepared by acid extracting alumina from an initial mordenite composition having a silica to alumina mole ratio of about 12:1 to 30:1 and a metal component selected from the group consisting of copper, silver, gold and zirconium.

The subject transalkylation reaction zone, however, preferably contains a catalyst similar to that described in U.S. Pat. No. 4,083,886. It is characterized by a method of preparation wherein a zeolite having a mordenite crystal structure and a sodium content of less than about 5 wt. % as $Na_2O$ is subjected to an aqueous ammoniacal treatment at a pH of at least about 9.5 and calcined in intimate admixture with a refractory inorganic oxide. This is a nonnoble metal catalyst, a term which is intended to indicate the catalyst does not contain ruthenium, rhodium, palladium, osmium, iridium or platinum or any combination of these metals at a concentration greater than 0.1 wt. %. Preferably, the catalyst contains essentially none of these metals except for unintentional contaminants.

The catalyst must be free of any component which provides a "metal function" to provide a high quality benzene product. The catalyst should therefore be free of such elements as the Group IB or VIB metals such as copper, chromium, molybdenum or tungsten. The catalyst should also be free of the Group VIII metals such as iron, cobalt and nickel. The presence of even small amounts of the transition metals is considered undesirable as they tend to promote the hydrogenation of aromatics. The total concentration of all metals in the catalyst should be less than 0.10 wt. percent. A catalyst containing less than this amount of total metals is referred to herein as "nonmetal" or metal-free catalyst.

The paraxylene separation zone may use any one of several different separation techniques such as fractionation, crystallization or selective adsorption to remove paraxylene from the stream of mixed xylenes which enters the paraxylene separation zone. The preferred paraxylene separation zone contains a bed of molecular sieves operated in accordance with the teaching of U.S. Pat. No. 3,201,491 to simulate the use of a continuously moving bed of molecular sieves. Subsequent improvements to the process are described in U.S. Pat. Nos. 3,696,107 and 3,626,020. The preferred paraxylene separation zone is therefore operated at adsorption conditions which include temperatures in the range of from 30 to about 300 degrees Centigrade, but preferably from 40 degrees to 250 degrees Centigrade. This zone may operate with either vapor phase or liquid phase process streams, with liquid phase operations being preferred. Pressures utilized may vary from atmospheric to about 1,000 psig, with more moderate pressures of from about 100 to 300 psig being preferred.

It is preferred that the molecular sieves are contained in one or more vertical columns, with the inlet and outlet positions of the feed stream, raffinate stream, extract stream and desorbent stream being periodically and unidirectionally shifted to simulate a continuous countercurrent moving bed of the adsorbent. The effluent streams of the adsorbent bed are fractionated as necessary to remove contaminants introduced by these changes in the inlet and outlet locations. The desorbent utilized in the process is recovered during this fractionation and recycled to the bed of adsorbent. This results in a continuous process which produces a xylene product stream containing over 98% paraxylene. A more detailed description of this process is contained in an article entitled, "The Parex Process for Recovering Paraxylene" which appeared at page 70 of *Chemical Engineering Progress*, Vol. 66, No. 9, Sept., 1970. Further details on the operation of the preferred paraxylene separation zone may also be obtained from U.S. Pat. Nos. 4,039,599 and 4,184,943. The paraxylene separation zone may depart from this preferred mode of operation through the use of batch-type operations or a true moving bed of solid adsorbent. The simulated cocurrent adsorptive separation process of U.S. Pat. No. 4,402,832 may also be employed. The extract and raffinate may be recovered as described in these references or as described in U.S. Pat. No. 4,381,419.

The preferred adsorbent is a "molecular sieve" type adsorbent chosen from various natural and synthetic aluminosilciate adsorbents which exhibit an ability to preferentially adsorb selected xylene isomers. Preferred for use in the separation zone are synthetically prepared type X and type Y zeolites containing selected cations at the exchangeable cationic sites within the crystal structure. One suitable molecular sieve is a cationexchanged type X or type Y zeolite containing a single cation selected from potassium, barium, sodium and silver. A second suitable molecular sieve is a type X or type Y zeolite containing both a first cation chosen from the group consisting of potassium, rubidium, cesium, barium and silver, and a second cation selected from the group consisting of lithium, sodium, magnesium, calcium, strontium, beryllium, cadmium, cobalt, nickel, copper, manganese and zinc. These molecular sieves are described in greater detail in U.S. Pat. No. 3,626,020. Other adsorbents, including those not yet developed, could be used if they meet the criteria of adequate selectivity and longevity necessary for commercial operation. Two other adsorbents which are suitable for paraxylene separation are described in U.S. Pat. Nos. 3,943,183 and 3,943,184.

I claim as my invention:

1. A process for the production of a desired xylene isomer which comprises the steps of:
   (a) passing a hereinafter characterized first process stream, which comprises at least two xylene isomers, into an adsorptive xylene separation zone, withdrawing a product stream comprising the desired xylene isomer from the xylene separation zone and also withdrawing a raffinate steam comprising an undesired xylene isomer from the xylene separation zone;
   (b) passing a first feed stream comprising toluene, a hereinafter characterized recycle stream and at least a portion of the undesired xylene isomer content of the raffinate stream into a catalytic transalkylation zone containing a nonmetal transalkylation catalyst and operated at high severity conditions including a hydrogen to hydrocarbon mole ratio above 2:1 and a temperature over 426 degress Centigrade, and forming a transalkylation zone effluent stream which comprises benzene, toluene, xylenes and $C_9$ aromatics;
   (c) separating the transalkylation zone effluent stream by fractional distillation to yield a benzene-rich process stream which is withdrawn from the process as a product stream, a toluene-rich process stream, a xylene-rich process stream comprising two xylene isomers, and a second process stream comprising $C_9$ aromatics;

(d) recycling at least a portion of the toluene-rich process stream into the transalkylation zone as said recycle stream; and (e) passing at least a portion of the xylene-rich process steam into the xylene separation zone as said first process stream.

2. The process of claim 1 further characterized in that at least a portion of the second process stream, which comprises $C_9$ aromatics, is recycled to the transalkylation zone.

3. The process of claim 2 further characterized in that orthoxylene is recovered from the xylene-rich process stream by fractional distillation.

4. The process of claim 3 further characterized in that a catalyst comprising a zeolite having mordenite structure is employed in the transalkylation zone.

5. The process of claim 1 further characterized in that xylenes derived from a second feed stream are passed into the xylene separation zone.

6. The process of claim 5 further characterized in that the desired xylene isomer is paraxylene.

7. A process for the production of a desired xylene isomer which comprises the steps of:

(a) passing a first feed stream comprising at least 35 mole percent toluene, a hereinafter characterized first process stream, which comprises at least one xylene isomer, and a hereinafter characterized recycle stream which comprises toluene into a catalytic transalkylation zone which contains a nonmetal transalkylation catalyst and is operated at high severity translkylation conditions including a temperature over 426 degrees Centigrade and a hydrogen to hydrocarbon mole ratio above 2:1, and producing a transalkylation zone effluent stream which comprises benzene, toluene, xylenes, and $C_9$ aromatics;

(b) separating the transalkylation zone effluent stream by fractional distillation in a fractional distillation zone and producing a benzene-rich process stream, a toluene-rich process stream, a xylene-rich process steam and a second process stream, which comprises $C_9$ aromatics;

(c) removing at least a portion of the benzene-rich process stream as a first product stream;

(d) returning at least a portion of the toluene-rich process stream to the transalkylation zone as the previously referred to recycle stream;

(e) passing the xylene-rich process stream into an adsorptive xylene separation zone and producing a second product stream, which comprises paraxylene, and a separation zone raffinate stream, which comprises an undesired xylene isomer;

(f) passing at least a portion of the raffinate stream into the transalkylation zone as at least a portion of the first process stream and, (g) passing at least a portion of the second process stream into the transalkylation zone.

8. The process of claim 7 further characterized in that orthoxylene is recovered from the transalkylation zone effluent stream by fractional distillation.

9. The process of claim 7 further characterized in that a catalyst comprising a zeolite having a mordenite structure is employed as the transalkylation catalyst.

10. The process of claim 9 further characterized in that a second feed stream comprising paraxylene and metaxylene is passed into the fractional distillation zone.

11. The process of claim 10 further characterized in that the second feed stream and the first feed stream are withdrawn from a fractionation column which is charged a mixture of $C_7$ to $C_9$ alkylaromatic hydrocarbons.

12. The process of claim 7 further characterized in that the transalkylation zone is operated at a temperature greater than 438 degrees Centigrade.

13. The process of claim 12 further characterized in that at least 15 mole percent of the total hydrocarbons charged to the process is toluene.

* * * * *